United States Patent [19]

Mohl et al.

[11] Patent Number: 4,934,996
[45] Date of Patent: Jun. 19, 1990

[54] PRESSURE-CONTROLLED INTERMITTENT CORONARY SINUS OCCLUSION APPARATUS AND METHOD

[75] Inventors: Werner Mohl, Vienna, Austria; Marc J. Tolkoff, Brookline, Mass.

[73] Assignee: Boston Scientific Corporation, Watertown, Mass.

[21] Appl. No.: 824,721

[22] Filed: Jan. 31, 1986

Related U.S. Application Data

[63] Continuation-in-part of Ser. No. 583,753, Feb. 27, 1984, abandoned.

[51] Int. Cl.⁵ .............................................. A61B 19/00
[52] U.S. Cl. .................................................... 600/17
[58] Field of Search ................ 128/1 D, 662-663, 128/673-674; 604/49, 96, 99

[56] References Cited

U.S. PATENT DOCUMENTS

| | | | |
|---|---|---|---|
| 3,064,649 | 11/1962 | Fuson | 128/400 |
| 3,132,643 | 5/1964 | Baum et al. | 128/672 |
| 3,425,419 | 2/1969 | Dato | 128/400 |
| 3,468,631 | 9/1969 | Raible et al. | 128/400 |
| 3,498,290 | 3/1970 | Shaw et al. | 128/663 |
| 3,610,228 | 10/1971 | Temkin | 128/673 |
| 3,692,018 | 9/1972 | Goetz et al. | 128/1 R |
| 3,738,372 | 6/1973 | Shioshvilli | 128/400 |
| 3,847,142 | 11/1974 | Williams, Jr. et al. | 128/694 |
| 3,923,060 | 12/1975 | Ellinwood | 128/DIG. 13 |
| 3,939,820 | 2/1976 | Grayzel | 128/1 D |
| 3,951,140 | 4/1976 | Eggleton et al. | 128/24 A |
| 3,985,123 | 10/1976 | Herzlinger | 128/1 D |
| 3,995,623 | 12/1976 | Blake et al. | 128/642 |
| 4,016,871 | 4/1977 | Schiff | 128/1 D |
| 4,051,840 | 10/1977 | Kantrowitz et al. | 128/1 D |
| 4,080,966 | 3/1978 | McNally et al. | 128/673 |
| 4,146,029 | 3/1979 | Ellinwood | 128/903 |
| 4,175,264 | 11/1979 | Schiff | 128/1 D |
| 4,190,057 | 2/1980 | Hill et al. | 128/675 |
| 4,259,961 | 4/1981 | Hood | 128/400 |
| 4,299,226 | 11/1981 | Banka et al. | 128/344 |
| 4,425,920 | 1/1984 | Bourland et al. | 128/672 |
| 4,427,009 | 1/1984 | Wells et al. | 128/400 |
| 4,456,000 | 6/1984 | Schjeldahl et al. | 128/1 D |
| 4,459,977 | 7/1984 | Pizon et al. | 128/1 D |

FOREIGN PATENT DOCUMENTS

381108 2/1981 Austria.

OTHER PUBLICATIONS

Sun et al., I "Characterization of the reactive hyperemic response time during intermittent coronary occlusion", Abstract presented in Vienna, Austria, (Feb. 2–5, 1986).
Sun et al., II, "Pattern recognition of CSP waveform", Abstract presented in Vienna, Austria, (Feb. 2–5, 1986).
Gundry, "Modification of Myocardial Ischemia in Normal and Hypertrophied Hearts Utilizing Diastolic Retroperfusion of the Coronary Veins", Journal of Thoracic Cardiovascular Surgery, 1982, vol. 83, No. 5, pp. 659–669.

(List continued on next page.)

Primary Examiner—William E. Kamm
Attorney, Agent, or Firm—Fish & Richardson

[57] ABSTRACT

The coronary sinus is intermittently occluded by use of means for occluding the sinus, a pressure transducer for sensing the fluid pressure within the sinus and providing corresponding fluid pressure signals, and a controller responsive to the transducer and arranged to provide trigger signals to the occluding means to trigger an occlusion and to interrupt the occlusion, the system being characterized in that the controller is arranged to estimate a plateau level of the fluid pressure during each occlusion and for providing a trigger signal to interrupt each occlusion on the basis of the estimate. The duration of the interruption before the next occlusion is controlled in response to the volume flow in the sinus during the interruption. Pharmacological agents are injected into the sinus during the occlusion, for retroprofusion to the heart tissue. An analysis of heart function is obtained by analyzing the local pressure maxima in successive heartbeats during occlusion. Initiation of the next occlusion is time based on fluid pressure signals taken from the sinus during occlusion. The degree of tissue at risk of infraction (or the amount of infarcted tissue) is estimated based on the fluid pressure signals.

39 Claims, 12 Drawing Sheets

OTHER PUBLICATIONS

Glogar, Mohl, et al., "Pressure-Controlled Intermittent Coronary Sinus Occlusion Reduces Myocardial Necrosis", *Abstracts of American Journal of Cardiology*, vol. 49, Mar. 1982, p. 1017.

Geary et al., "Quantitative Assessment of Infarct Size Reduction by Coronary Venous Retroperfusion in Baboons", *The American Journal of Cardiology*, vol. 50, Dec. 1982, pp. 1424-1430.

Berdeaux et al., "Effects of Diastolic Synchronized Retroperfusion on Regional Coronary Blood Flow in Experimental Myocardial Ischemia", *American Journal of Cardiology*, May 1981, vol. 47, p. 1033.

Mohl et al., "Effects of Intermittent Coronary Sinus Occlusion (ICSO) on Tissue Parameters After Ligation of LAD", 11th Europ. Conf. Microcirculation, 1980, No. 20, pp. 517-520.

Farcot et al., "New Catheter-Pump System for Diastolic Synchronized Coronary Sinus Retroperfusion", *Medical Progress Through Technology*, Spring, 1980, p. 29.

Deboer et al., "Autoradiographic Method for Measuring the Ischemi Myocardium at Risk: Effects of Verapamil on Infarct Size After Experimental Coronary Artery Occlusion", *Proc. Natl. Acad. Sci. U.S.A.*, vol. 77, No. 10, Oct. 1980, pp. 6119-6123.

Farcot et al., "Synchronized Retroperfusion of Coronary Veins for Circulatory Support of Jeopardized Ischemic Myocardium", *American Jounral of Cardiology*, Jun. 1978, p. 1191.

Arealis et al., "Attempts to Increase the Blood Supply to an Accutely Ischemic Area of the Myocardium by Intermittent Occlusion of the Coronary Sinus", (Preliminary Results), *Medical Research Engineering*, Dec. 4, 1977, pp. 4-7.

Meerbaum et al., "Diastolic Retroperfusion of Acutely Ischemic Myocardium", *The American Journal of Cardiology*, vol. 37, Mar. 31, 1976, pp. 587-598.

Lie et al., "Macroscopic Enzyme-Mapping Verification of Large, Homogeneous, Experimental Myocardial Infarcts of Predictable Size and Location in Dogs", *J. thoracic Cardiovascular Surgery*, vol. 69, 1975, pp. 599-605.

Moll, "Revaskularisation des ischamischen Herzmuskels bei disseminierter Koronarsklerose", *Zschr. inn. Med.*, Jahrg. 30, 197, Heft 1, pp. 10-14.

Arealis et al., "Arterialization of the Coronary vein Coming from an Ischemic Area", Chest, vol. 63, No. 3, Mar. 1973, pp. 462-463.

Muers et al., "The Reflex Cardiovascular Depression Caused by Occlusion of the Coronary Sinus in the Dog", *Journal of Physiology*, 1972, vol. 221, pp. 259-282.

Tiedt et al., "The Dynamics of the Coronary Venous Pressure in the Dog", Pflungers Archive 288, 1966, pp.

Thornton et al., "Effect of Chronic Cardiac Venous Occlusion on Coronary Arterial and Cardiac Venous Hemodynamics", *American Journal of Physiology*, vol. 128, 1959, pp. 179-184.

Bakst et al., "Arterialization of the Coronary Sinus in Occlusive Cornary Artery Disease", *J. Thoracic Surgery*, vol. 31, May 1956, pp. 559-568.

Eckstein et al., "Acute Effects of Elevation of Coronary Sinus Pressure", *Circulation*, vol. VII, Mar. 1953, pp. 422-436.

Hahn et al., "Revascularization of the Heart", *Circulation*, vol. V, Jun. 1952, pp. 810-815.

Beck, "Revascularization of the Heart", *Surgery*, Jul. 1949, vol. 26, No. 1, pp. 82-87.

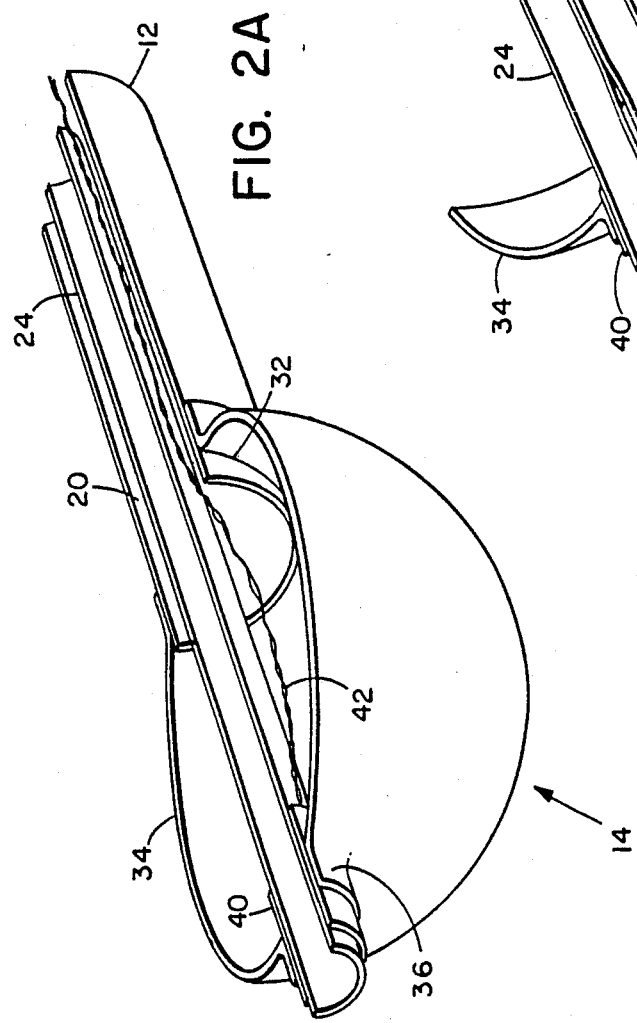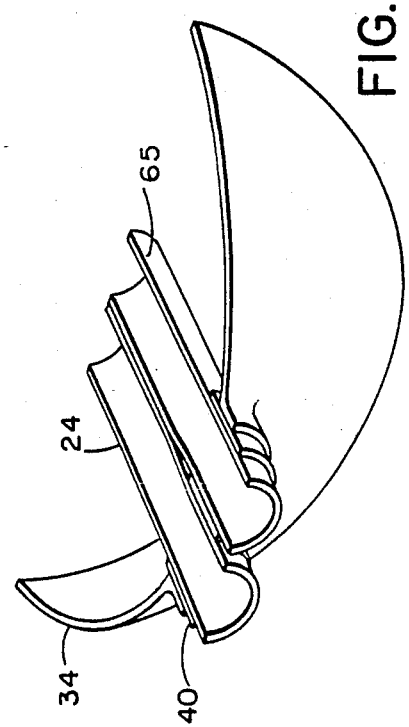

PRESSURE-CONTROLLED INTERMITTENT CORONARY SINUS OCCLUSION APPARATUS AND METHOD

BACKGROUND OF THE INVENTION

This application is a continuation-in-part of Mohl et al., U.S. patent application Ser. No. 583,753, filed Feb. 27, 1984, now abandoned.

This invention relates to intermittent periodic occlusion of the coronary sinus in order to accomplish retroperfusion, i.e., repeatedly temporarily blocking the major vein which collects blood from the heart muscle in order to cause venous blood to flow back from the normal contracting myocardium to reach ischemic portions of the heart muscle.

Arterial blood which feeds the heart muscle is able to pass through and nourish healthy heart tissue, but has difficulty in reaching the ischemic tissue. This reduces the delivery of nutrients to, and the carrying away of the waste products of metabolism (metabolites) from, the ischemic tissue.

It has been proposed to reach the ischemic tissue by causing blood to flow in a reverse direction from the coronary sinus back through the coronary veinous system. Such retroperfusion has been attempted by feeding blood into the coronary sinus from another source, either by permanently connecting an artery to the coronary sinus or by temporarily inserting into the sinus a catheter supplied with blood which has been taken from a remote artery and passed through a blood pump outside the patient's body.

Another proposed technique for retroperfusion uses an inflatable balloon held on the end of a catheter to intermittently occlude the coronary sinus. Blood pressure in the sinus then rises as the heart beats so that blood received in the sinus through the healthy tissue of the heart muscle is forced back into the ischemic tissue. In such intermittent coronary sinus occlusion the balloon end of the catheter is inserted percutaneously or intraoperatively. The other end of the catheter is supplied with gas or liquid by a pump which can be controlled to cause the balloon to inflate and deflate cyclically, for example at a rate synchronized with the heart pulse rate, or on the basis of pressure.

SUMMARY OF THE INVENTION

In general, the invention concerns an improvement that leads to making intermittent occlusion of a coronary sinus a successful and useful technique. The invention employs means for occluding the sinus, a pressure transducer for sensing the fluid pressure within the sinus and providing corresponding fluid pressure signals, and a controller responsive to the transducer and arranged to provide trigger signals to the occluding means to trigger an occlusion and to interrupt the occlusion. In one aspect, the invention is characterized in that the controller is arranged to estimate a plateau level of the fluid pressure during each occlusion and to provide the trigger signals to interrupt each occlusion on the basis of said estimate.

The invention is found to provide sufficient retroperfusion flow to effectively wash toxic metabolites and edema from the ischemic tissue while minimizing damage to healthy tissue. Heart contractability can be improved. The invention may be used in bolstering heart function during heart surgery and catheterization, especially in combination with conventional pharmacological agents.

In preferred embodiments, each occlusion is interrupted before the fluid pressure reaches the plateau level; the plateau value is estimated in real time during each period of occlusion based on exponential curve fitting; the controller includes sampling circuitry for sensing the fluid pressure signals, e.g., by storing the sensed signals at a rate substantially higher than the heartbeat rate, first analysis circuitry for determining and storing a local maximum value of the pressure for each heartbeat from the stored sensed signals, second analysis circuitry for estimating in real time the plateau level from the stored local maximum values, and comparison circuitry for comparing a predetermined percentage of the estimated plateau level with successive local maximum values, and generating trigger signals for triggering interruption of each occlusion at a time dependent on the result of the comparison; the predetermined percentage is greater than 90%, preferably 94%; and the occluding means includes an inflatable element in the sinus, and a pump for selectably inflating the inflatable element.

In another aspect, the invention features use of a sensor for delivering flow signals indicative of the volume flow of fluid in the sinus during periods when the occlusion is being interrupted, and the controller is arranged to trigger the initiation of the next occlusion at a time determined by the flow signals. The desirable effects of retroperfusion and washout thus can be optimized consistent with maintaining adequate coronary arterial flow.

In preferred embodiments, the flow signals represent velocity of flow, or fluid pressure as a function of time; the point at which to restart occlusion is accurately determined in real time during each period of interruption; the controller employed includes sampling circuitry for sampling the flow signals and storing the samples, analysis circuitry for determining from the stored samples the time when the peak of the flow occurs during each period of interruption of the occlusion, and trigger circuitry for delivering a trigger signal to trigger the next occlusion at a time determined by when the peak occurs; and the time of start of occlusion is after the occurrence of maximum flow in the coronary sinus.

In another aspect, the invention features recording and displaying the pressure maxima for the succession of heartbeats that occur during an occlusion to permit evaluation, e.g., in real time, of their relationship for indication of the state of health of the heart tissue. It is realized, for instance, that the rate of rise of the curve of maxima usually indicates the contractility of the heart, the steeper the rate of rise, the more contractile.

In another aspect, the invention features means, during the occlusion, for infusing a pharmacological agent into the sinus whereby the agent can be retroperfused to the heart tissue. In this manner cardioplegic and thrombolytic agents can reach ischemic tissue, e.g., during heart surgery.

In another aspect, the invention features a method for aiding analysis of heart function which includes the steps of occluding the coronary sinus, measuring the fluid pressure in the sinus, plotting the fluid pressure against time during the occlusion, and analyzing the successive local pressure maxima which occur in successive heartbeats during the occlusion.

In another aspect, the invention features triggering the initiation of the next occlusion at a time based on fluid pressure signals taken from the sinus during occlusion. As a result the start of the next occlusion can be delayed until the time when peak reactive hyperemia has occurred.

In preferred embodiments, the timing of the initiation of the next occlusion is based on a combination of parameters derived from successive pressure maxima and pressure minima. The pressure maxima and minima are fitted to exponential curves. The parameters include heart rate, the asymptotic plateaus of the exponential curves, and the time constants of the exponential curves.

In other aspects, the invention features analyzing the degree of tissue damage by estimating the amount of tissue at risk of infarction (or the amount of infarcted tissue) on the basis of fluid pressure signals taken within the sinus. Thus during the intermittent occlusion procedure, the amount of heart tissue at risk and the amount of tissue actually infarcted can be estimated.

In preferred embodiments, the estimation is based on local maxima and local minima of the fluid pressure signals.

Other advantages and features of the invention will be apparent from the following description of the preferred embodiment and from the claims.

DESCRIPTION OF THE PREFERRED EMBODIMENT

We first briefly describe the drawings.

Drawings

FIG. 2A is an isometric view, broken away, of the distal end of the catheter of FIG. 1.

FIG. 2B is an isometric view of an alternative embodiment of FIG. 2A.

STRUCTURE

Figure 1:
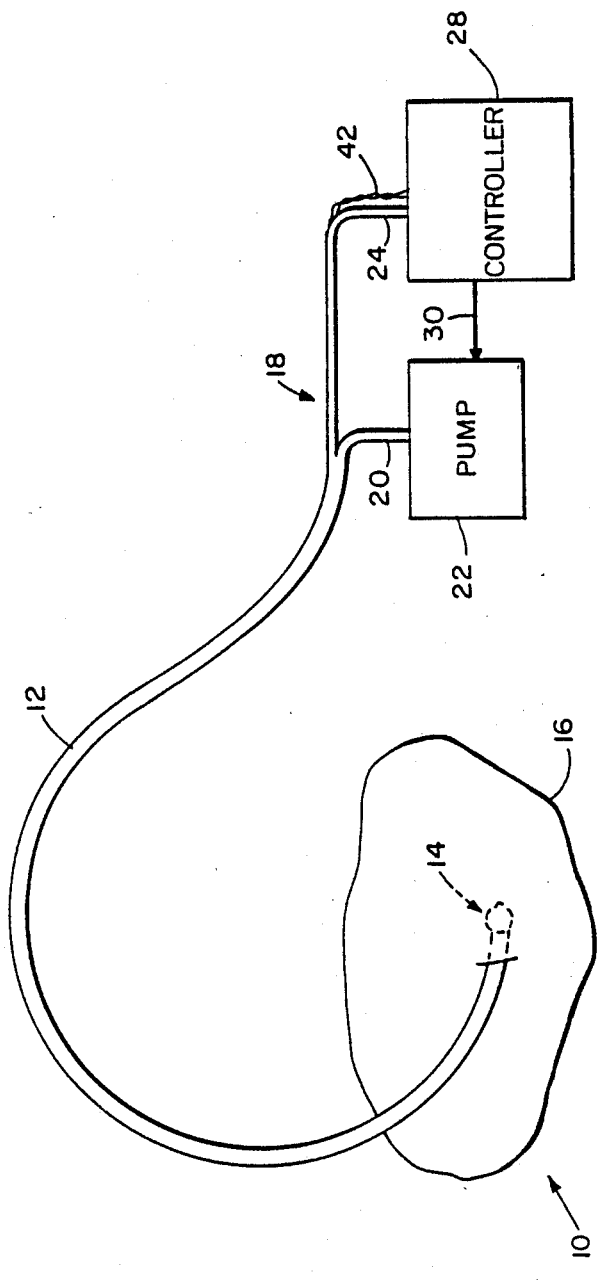
FIGS. 1 and 1A are a diagrammatic view of a heart with intermittent coronary sinus occlusion apparatus and associated flow charts.

Referring to FIG. 1, intermittent coronary sinus occlusion apparatus 10 includes multi-lumen catheter 12 having its distal end 14 inserted into the coronary sinus of heart 16 via the right atrium. The proximal end 18 of catheter 12 has a balloon inflation lumen 20 connected to pump 22. A second lumen 24, coaxial with lumen 20, and wires 42 are connected to controller 28 which contains circuitry for delivering control signals over line 30 to trigger the starting and stopping of pump 22.

Referring to FIG. 2A, at distal end 14 of catheter 12, lumen 20 communicates with inflatable balloon 34 via proximal aperture 32. Lumen 24 passes through the balloon and exits distally via aperture 36. Lumen 20 and balloon 34 contain gas delivered from pump 22.

The distal end of lumen 24 is open to the coronary sinus and holds a stationary column of isotonic heparinized saline solution with or without pharmacological agents. Changes in blood pressure in the sinus are transmitted to the proximal end of lumen 24, and are sensed at controller 28.

The distal end of lumen 24 is surrounded by an ultrasonic transducer 40 for sensing the flow of fluid in the sinus and delivering corresponding flow signals. Transducer 40 is connected to wires 42.

Referring to FIG. 2B, the catheter may include a third lumen 65 for carrying cardioplegic and thrombolytic (or other pharmacological) agents into the sinus for retroperfusion to the ischemic tissue. The delivery of the agents through lumen 65 may begin as soon as the balloon is inflated or may be triggered based on the trend of the local maxima during infusion.

Figure 3:
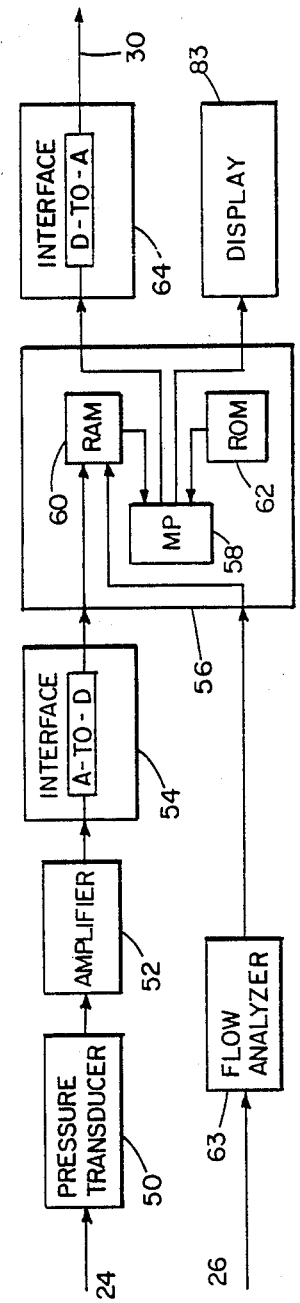
FIG. 3 is a block diagram of the controller of FIG. 1.

Referring to FIG. 3, controller 28 has a pressure transducer (or other pressure sensor) 50 attached to the proximal end of lumen 24 (for sensing the blood pressure in the coronary sinus and providing corresponding fluid pressure signals). Transducer 50 is connected through amplifier 52 and interface 54 (which includes an A-to-D converter) to processor 56. Processor 56 has microprocessor 58, RAM 60, and ROM 62 (which holds the program for processor 56). Processor 56 also has an input connected to flow analyzer 63, which includes Doppler circuitry for driving transducer 40 to vibrate ultrasonically and for detecting the Doppler shift of the resulting vibrations bouncing back to transducer 40 from blood flowing in the coronary sinus, thus to give an indication of flow velocity.

The output of processor 56 is connected through interface 64 (including a D-to-A converter) to line 30 which carries trigger signals to turn on and shut off pump 22.

Processor 56 is also connected to real time display 83 for displaying the sinus pressure over time for observation of the successive local pressure maxima as an indication of the state of health of the heart tissue, e.g., its contractility.

OPERATION

The distal end of catheter 12 is inserted, percutaneously or intraoperatively, into the coronary sinus. In operation, controller 56 issues a trigger signal through interface 64 and over line 30 to turn on pump 22. Gas is pumped into lumen 20 causing balloon 34 to inflate within the coronary sinus, blocking blood flow out of the sinus. Blood continues to flow into the sinus and retroperfuses back into the ischemic tissue.

Figure 4:
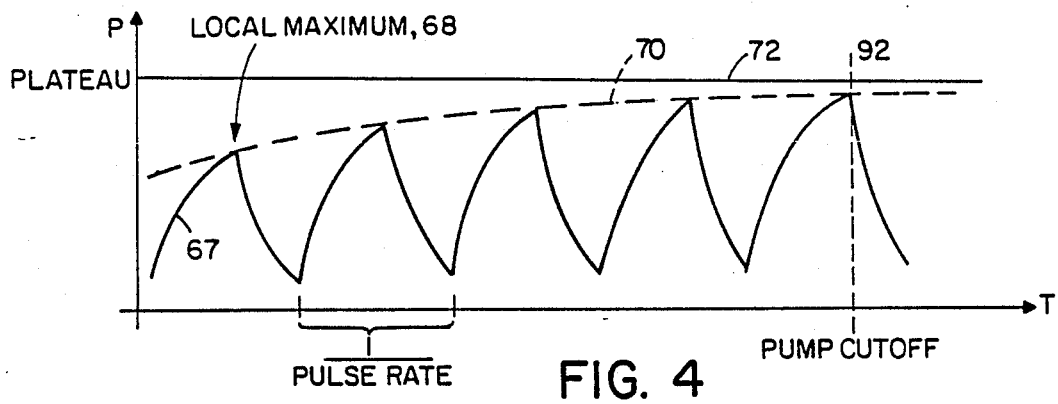
FIGS. 4, 7 is a representational graph of changes of coronary sinus pressure with time.

Referring to FIG. 4, with the sinus blocked, systolic pressure 67 varies cyclically with the heart pulse rate. For each heartbeat, pressure rises to a local maximum (e.g., 68), and then falls near to a base level, after which the cycle is repeated. The successive local maxima lie on a curve 70 which rises toward asymptotic plateau 72, e.g., 80 mm of Hg. With higher pressures, the retroperfused blood reaches more ischemic tissue, but the peak pressure for successive heartbeats rises approximately exponentially and we realize, accordingly, that the amount of additional tissue being reached in each successive heartbeat is not as great as in prior heartbeats. We also realize that a benefit of retroperfusion, the washout of metabolites, is dependent upon attainment of pressure, but not prolongation of pressure, at the ischemic site, while continuing to occlude the sinus once plateau 72 is reached could damage healthy heart tissue. According to the invention, controller 28 is arranged to terminate the occlusion on the basis of the predicted plateau, more specifically when the sinus pressure reaches a predetermined level (e.g., 94% of the predicted plateau).

Figure 1A:
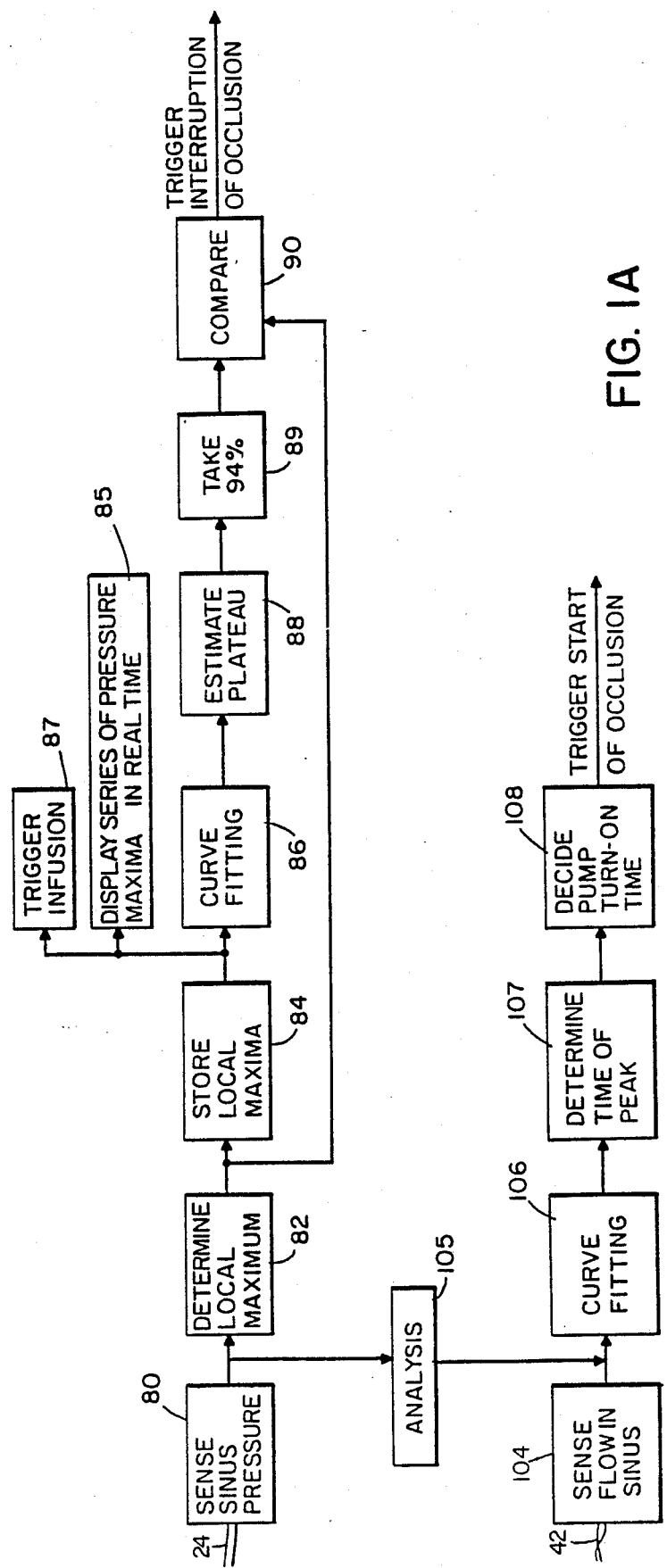

Referring again to FIG. 1 and to FIG. 1A, processor 56 samples (80) the output of interface 54 many times in each heart pulse cycle (e.g., at a rate of at least 2500 Hz) and stores the pressure samples in RAM 60. It then compares successive samples to determine the local maximum pressure for each heartbeat. Each local maximum is stored (84) in RAM 60. Processor 56 then performs a curve fitting routine (86), e.g., by regression analysis, in which the available local maxima are fitted to an exponential function of the form $P = A - Be^{-ct}$, where P is the pressure as a function of time, A is the plateau pressure, t is time and B the difference between the plateau and the base-line pressures, and c is the slope contant. From the resulting function, processor 56 estimates (88) the level that plateau 72 would have and calculates 94% of that plateau (89). Finally, processor 56 compares (90) each newly calculated local maximum with the 94% value and when a local maximum first reaches at least that 94% value, (e.g., at time 92 in FIG. 4) processor 56 triggers the pump to evacuate, or provide negative pressure to, lumen 20, thus interrupting the inflation of balloon 34 before the plateau is reached.

The local maxima can also be displayed in real time 85 in order to permit analysis of the condition of the heart tissue, and can be used as the basis for triggering an infusion of pharmacological agents 87.

Figure 5:
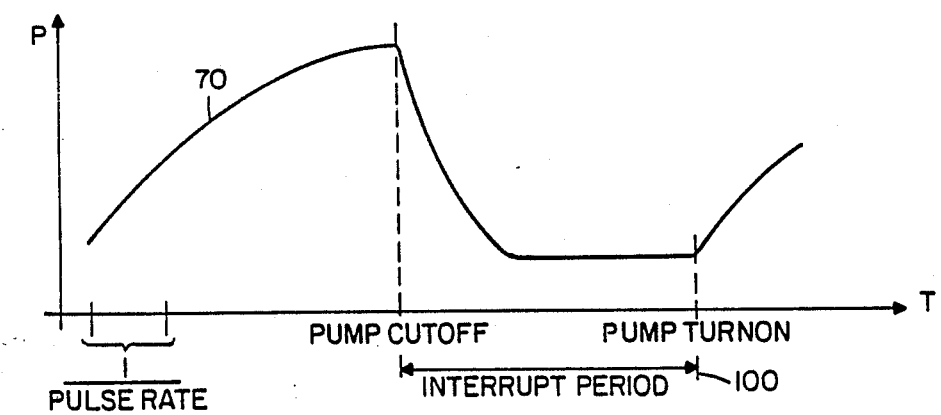
FIG. 5 is a representational graph of changes of coronary sinus pressure with time showing the interrupt period.

Referring to FIG. 5, after pump cutoff, the curve of the local pressure maxima falls off to its baseline level until, at time 100, the pump is turned on again and the cycle repeats.

During occlusion, the heart muscle vascular system is subjected to back pressure and accordingly is resiliently expanded. When pump 22 is shut off and the back pressure is relieved, the heart muscle resiliently relaxes by contracting, thus forcing blood, toxic metabolites, and water from the ischemic tissue into the coronary sinus.

How long the pump operation should be interrupted before initiating a subsequent occlusion depends on balancing the effect of maximum outwashing obtained by a longer interruption period with the effects of additional retroperfusion obtained by a shorter interruption period.

Figure 6:
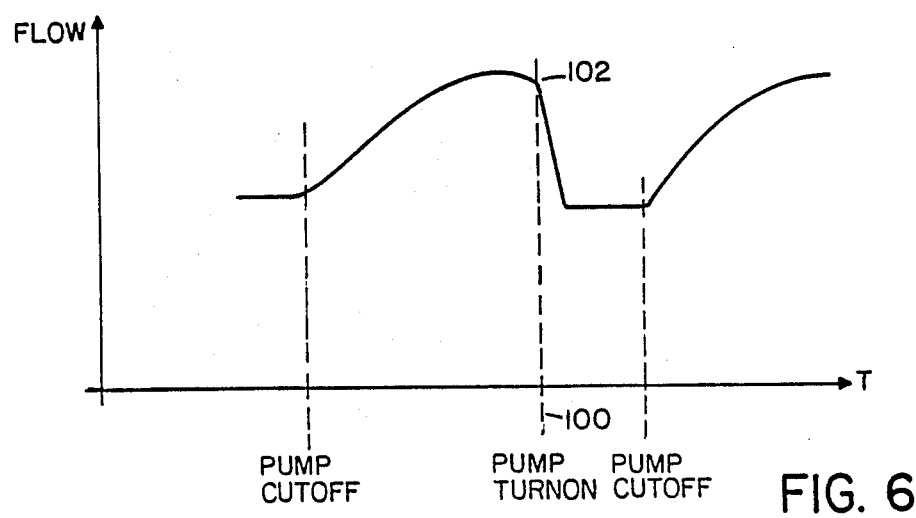
FIG. 6 is a representational graph of changes of coronary blood flow rate with time.

Referring to FIG. 6, the flow rate of blood in the sinus after occlusion has stopped rising exponentially to a peak value 102. By allowing the pump interruption to last at least until peak 102 is reached, the desirable effects of the intermittent occlusion can be optimized.

Referring again to FIG. 1 and FIG. 1A, this is accomplished by having processor 56 sample (104) the flow velocity signals delivered from flow analyzer 63, performing a curve fitting (106) of the samples to an exponential curve to determine (107) the peak flow 102, and triggering pump turn-on time (108) to occur after a predetermined brief period following the peak.

Other flow sensors can be used such as those which measure the resistance of a thermistor driven by a regulated current, as the sinus blood flows past the thermistor.

Alternatively, rather than measuring flow velocity, the flow volume in the sinus may be determined inferentially from the detailed sampling of sinus pressure with time (particularly during the period of a single heartbeat), using appropriate correlation analysis (105), as shown in FIG. 1.

Figure 7:
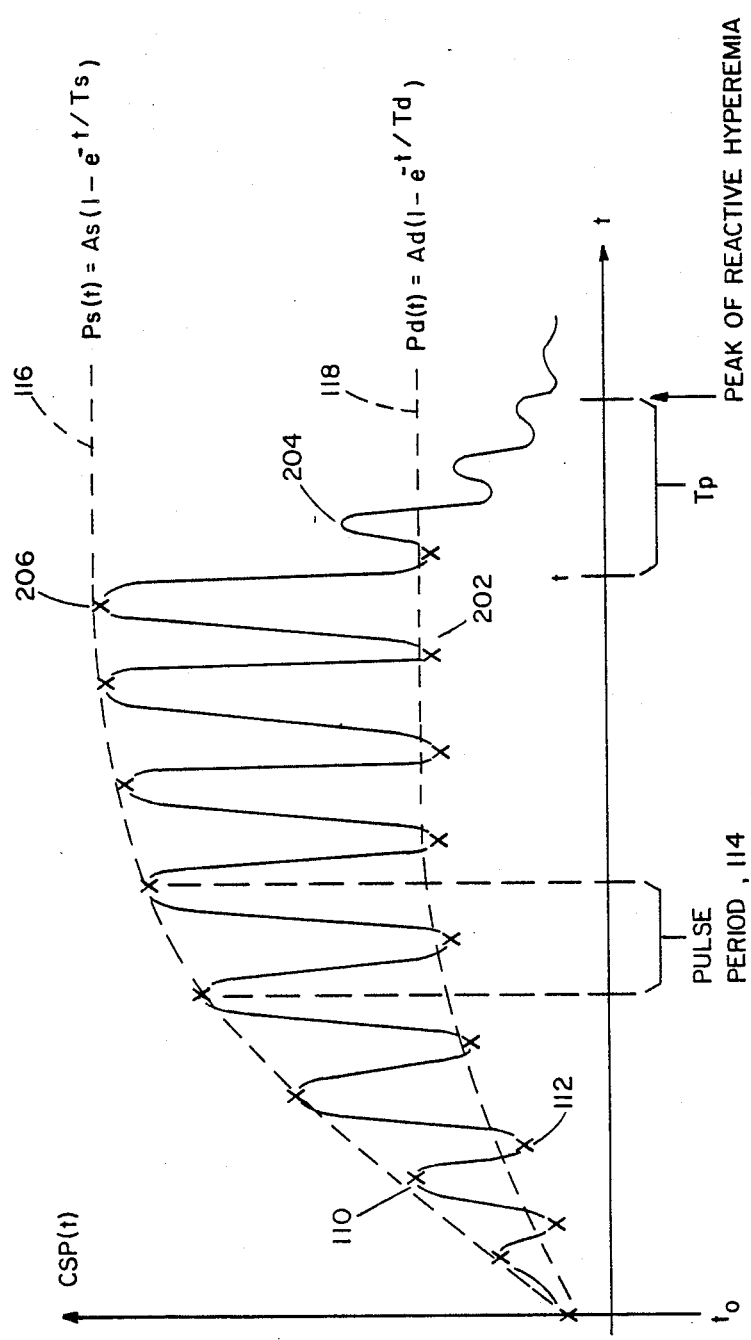
Figure 8:
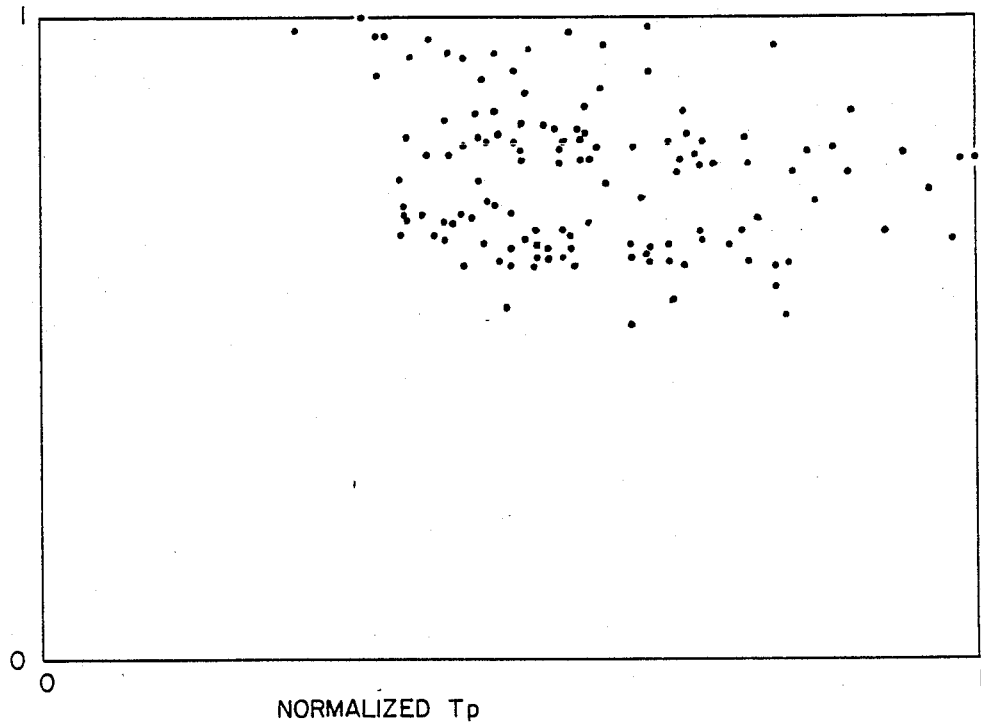
FIGS. 8 through 16 are graphs of normalized data points of various parameters versus the time of peak reactive hyperemia (Tp).

Alternatively, rather than measuring either flow velocity or flow volume, the time to begin occlusion (i.e., the time $T_p$ of peak reactive hyperemia corresponding to point 102 on FIG. 6) can be determined by measuring certain characteristics of the coronary sinus pressure curve, CSP(t), during the previous period of occlusion. Referring to FIG. 7, a typical plot of coronary sinus pressure against time, beginning at the onset of occlusion ($t_o$), exhibits a series of systolic pressure peaks 110 interleaved with a series of diastolic valleys 112. The pulse period 114 of the heartbeat is represented by the time between successive peaks or between successive valleys. The systolic pressure peaks can be fitted to an exponential curve 116 of the form $P_s(t) = A_s(1 - e^{-t/T_s})$ where $A_s$ is the asymptotic plateau of pressure maxima and $T_s$ is the time to reach the plateau. Similarly the diastolic pressure valleys can be fitted to an exponential curve 118 of the form $P_d(t) = A_d(1 - e^{-t/T_d})$ where $A_d$ is the asymptotic plateau of diastolic pressure valleys, and $T_d$ is the time to reach the plateau. $T_p$ represents the period between the termination of occlusion and the peak reactive hyperemia. $T_p$ can be estimated as $$T_p = -1.60\, T_s + 0.82\, T_d + 3.70\, T_s/T_d - 3.50\, T_d/T_s$$
$$-0.260\, A_s + 1.60\, A_d - 0.510\, A_s/A_d - 53.0\, A_d/A_s$$
$$-0.0081\, HR + 18.0\, RRI + 0.65\, A_s/RRI - 0.38\, A_d/RRI -$$
$$0.10\, T_s/RRI + 0.15\, T_d/RRI + 7.7$$

where HR is the heart rate, i.e., the reciprocal of the pulse period, and RRI is the reciprocal of the heart rate.

FIGS. 8–16 show the experimentally determined relationships between normalized $T_p$ and normalized values of HR, $T_s$, $T_s/T_d$, $T_d$, $T_d/T_s$, $A_s$, $A_d/A_s$, $A_d$, and $A_s/A_d$ in experiments with 12 dogs. The correlations represented by this data are

| | | |
|---|---|---|
| $T_s = -.21$ | $T_p + .49$; | $r = .11$ |
| $T_d = -.39$ | $T_p + 5.0$; | $r = .21$ |
| $T_s/T_d = 0.63$ | $T_p + .98$; | $r = .14$ |
| $T_d/T_s = -.060$ | $T_p + 1.1$; | $r = .18$ |
| $A_s = 0.46$ | $T_p + 62$; | $r = .003$ |
| $A_d = -.041$ | $T_p + 14$; | $r = .008$ |
| $A_s/A_d = -.074$ | $T_p + 5.1$; | $r = .046$ |
| $A_d/A_s = .0002$ | $T_p + .22$; | $r = .002$ |
| $HR = -.419$ | $T_p + 127$; | $r = .21$ |

Figure 17:
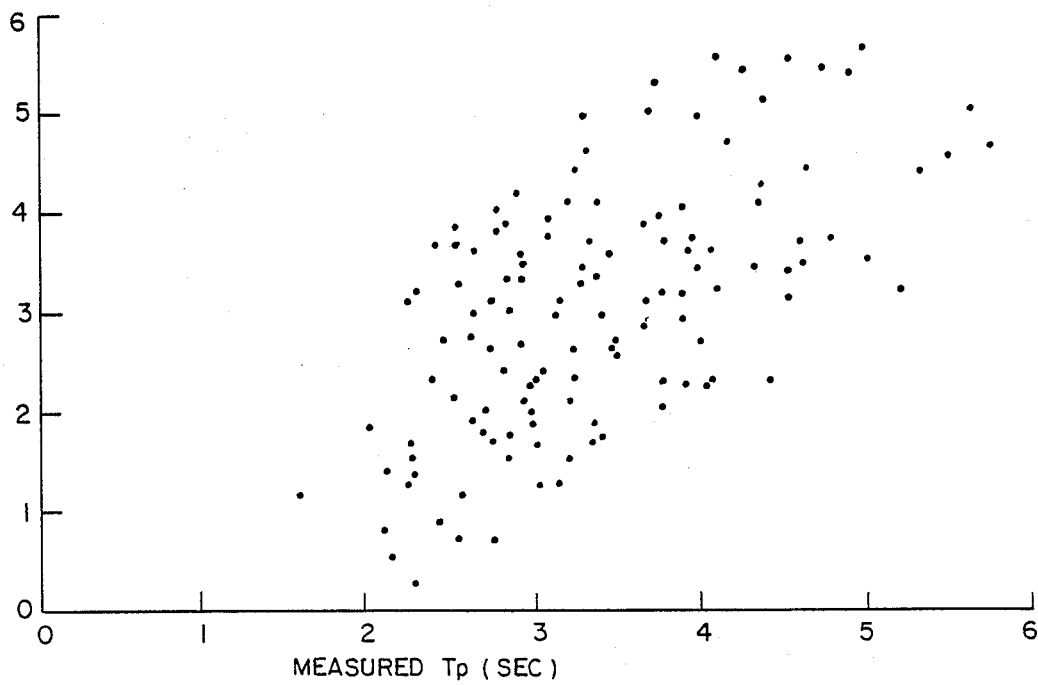
FIG. 17 is a graph of data points of predicted Tp versus measured Tp.
Figure 9:
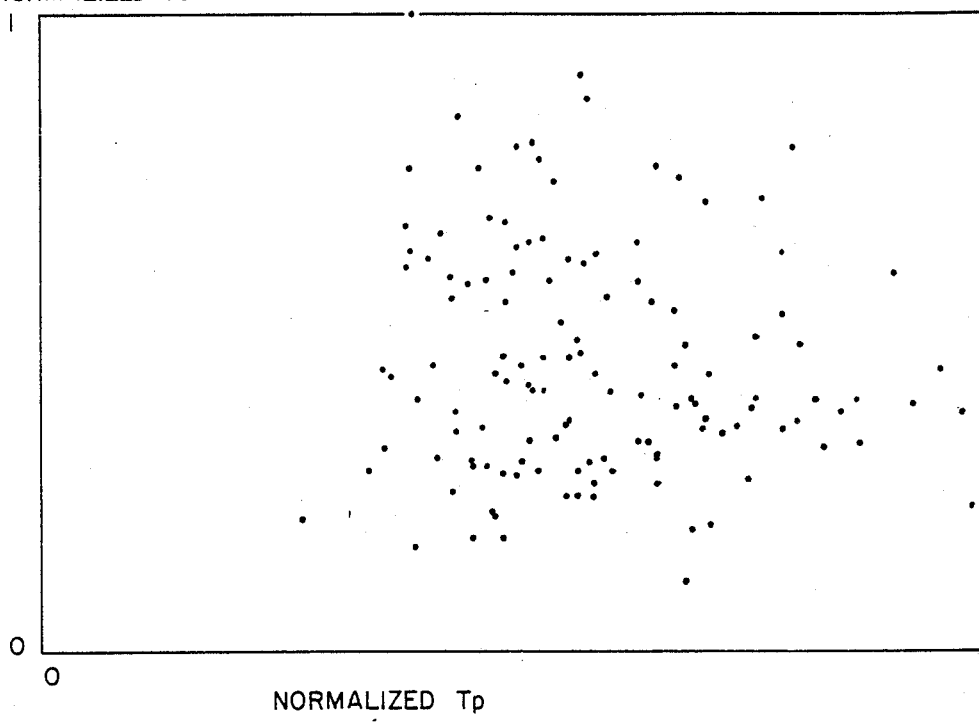
Figure 10:
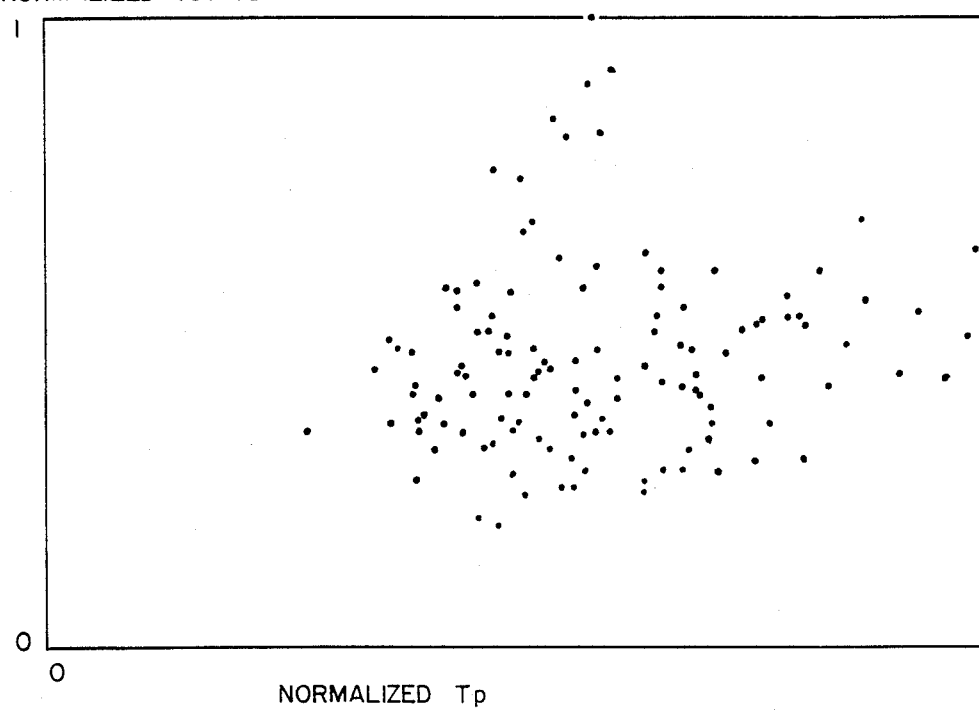
Figure 11:
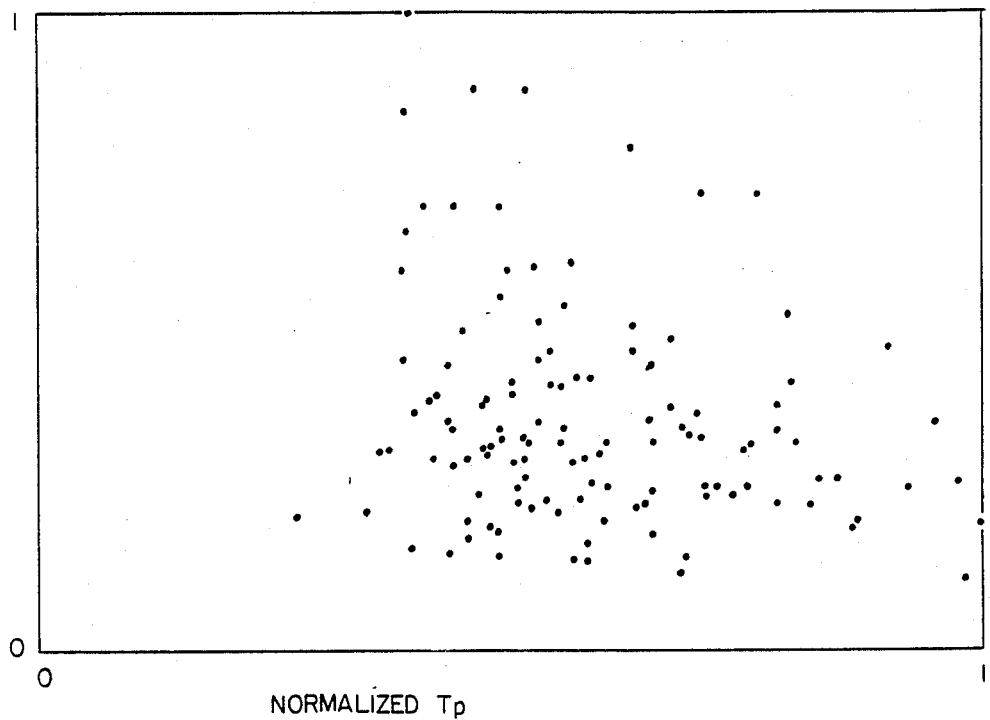
Figure 12:
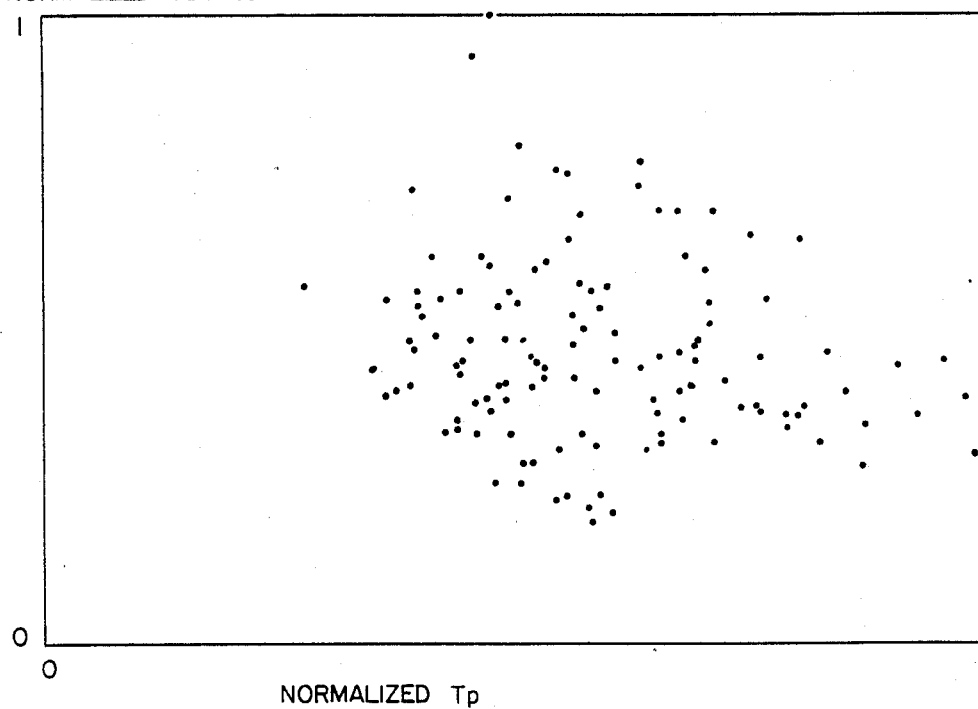
Figure 13:
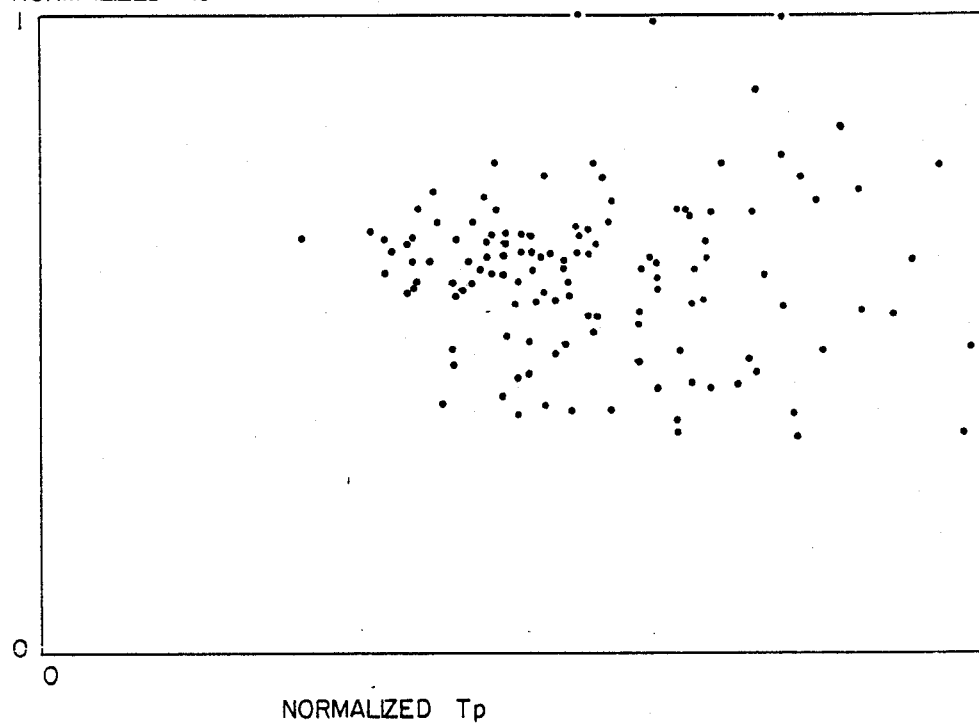
Figure 14:
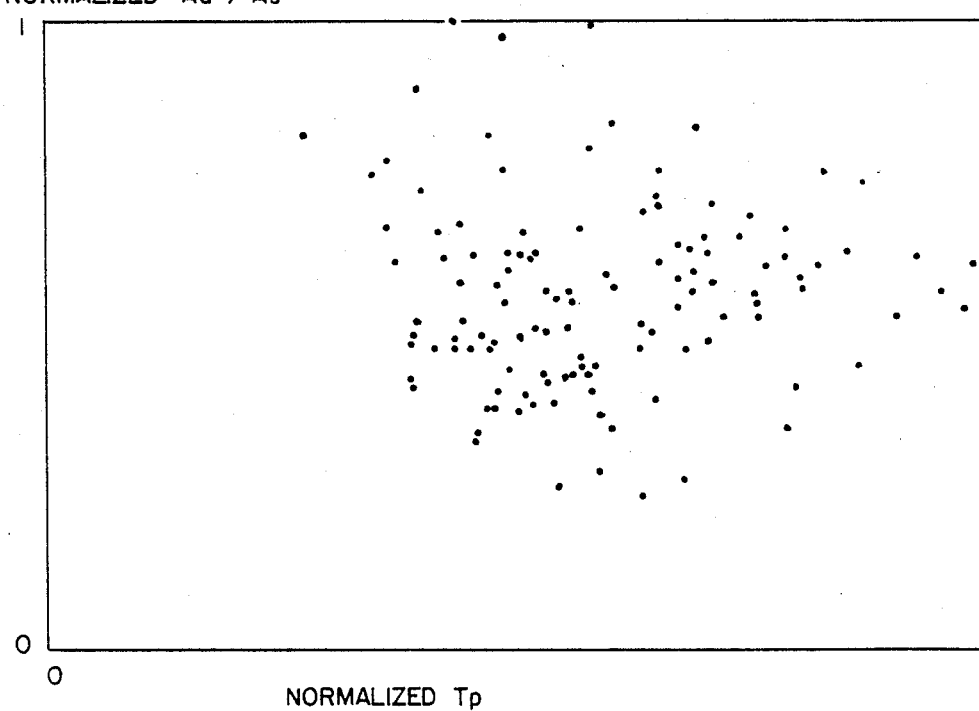
Figure 15:
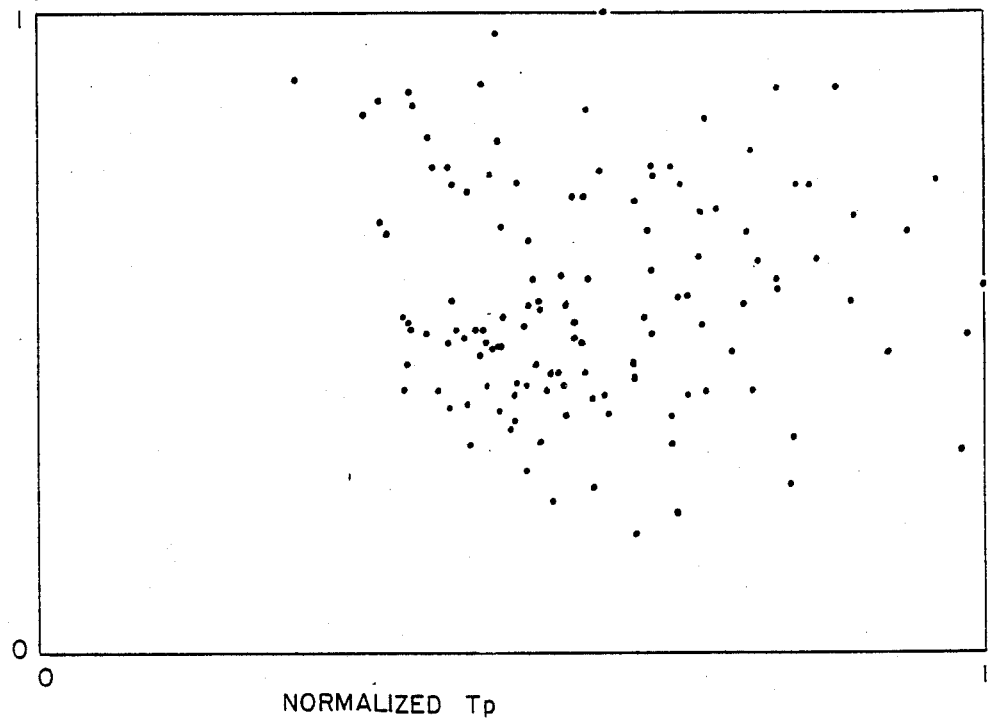
Figure 16:
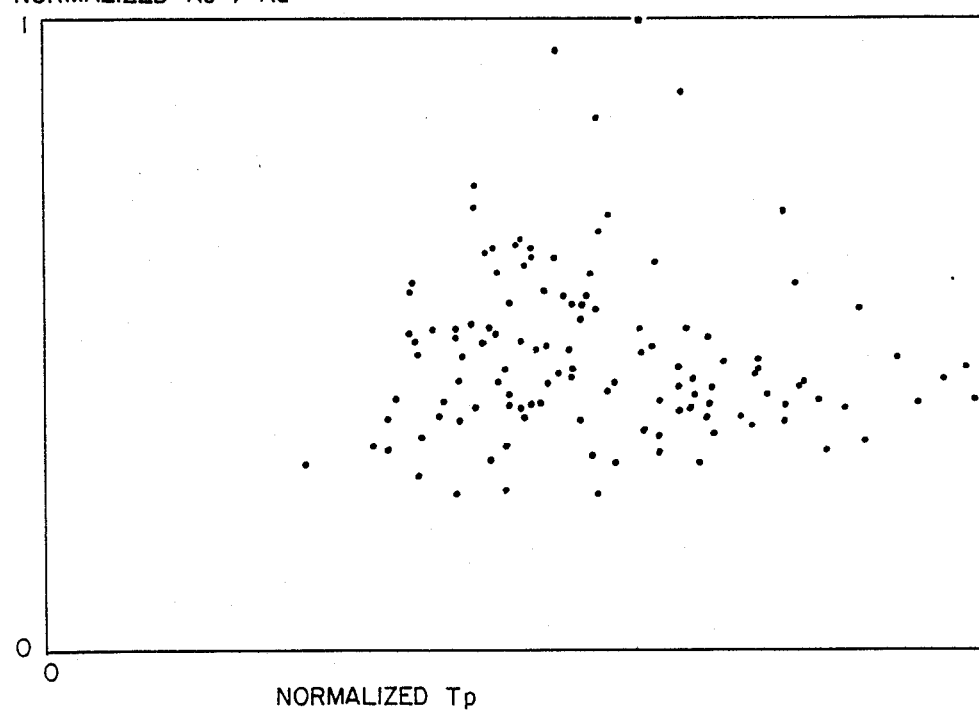

FIG. 17 shows the correlation between predicted $\hat{T}_p$ and measured $T_p$ in seconds. A linear regression between $\hat{T}_p$ and $T_p$ yields $$\hat{T}_p = 0.92\, T_p + 0.00;\ r = 0.634\ (P\ 0.001)$$

Measured $\hat{T}_p$ had a mean of 3.4 seconds (SD=0.9, n=128)

Figure 18:
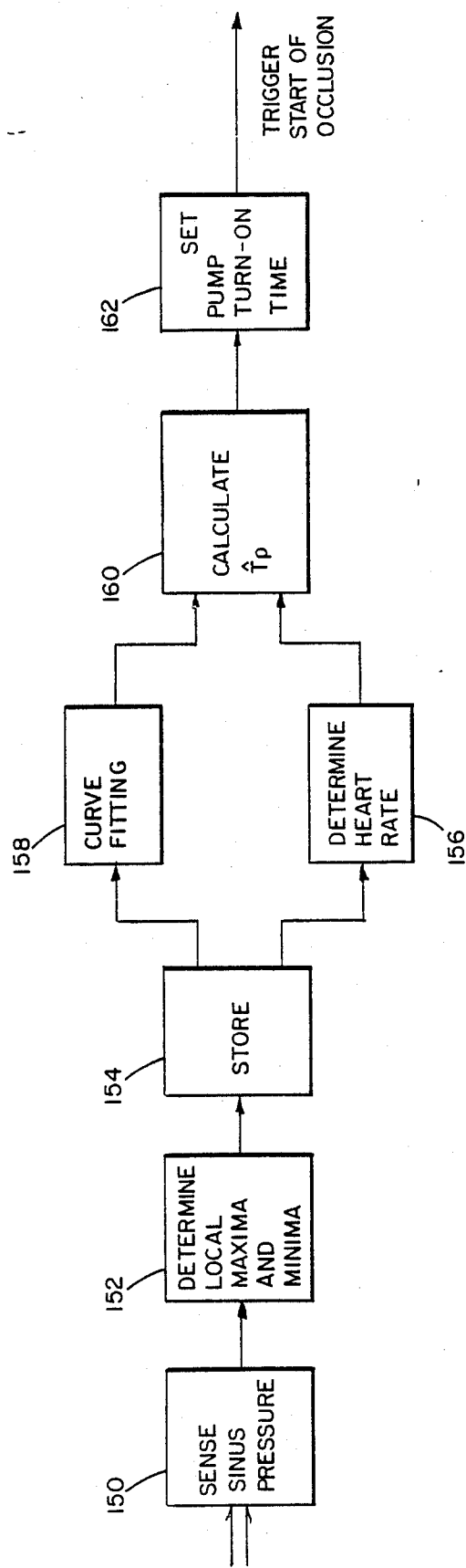
FIG. 18 is a flow chart of a procedure for triggering start of occlusion.

Referring to FIG. 18, the steps for triggering the start of occlusion include sensing sinus pressure 150, determining local systolic peaks (maxima) and diastolic valleys (minima) 152, storing the maxima and minima 154, determining heart rate 156, fitting the stored data to exponential curves 158, predicting $T_p$ 160, and deciding pump turn-on time 162 accordingly.

Figure 19:
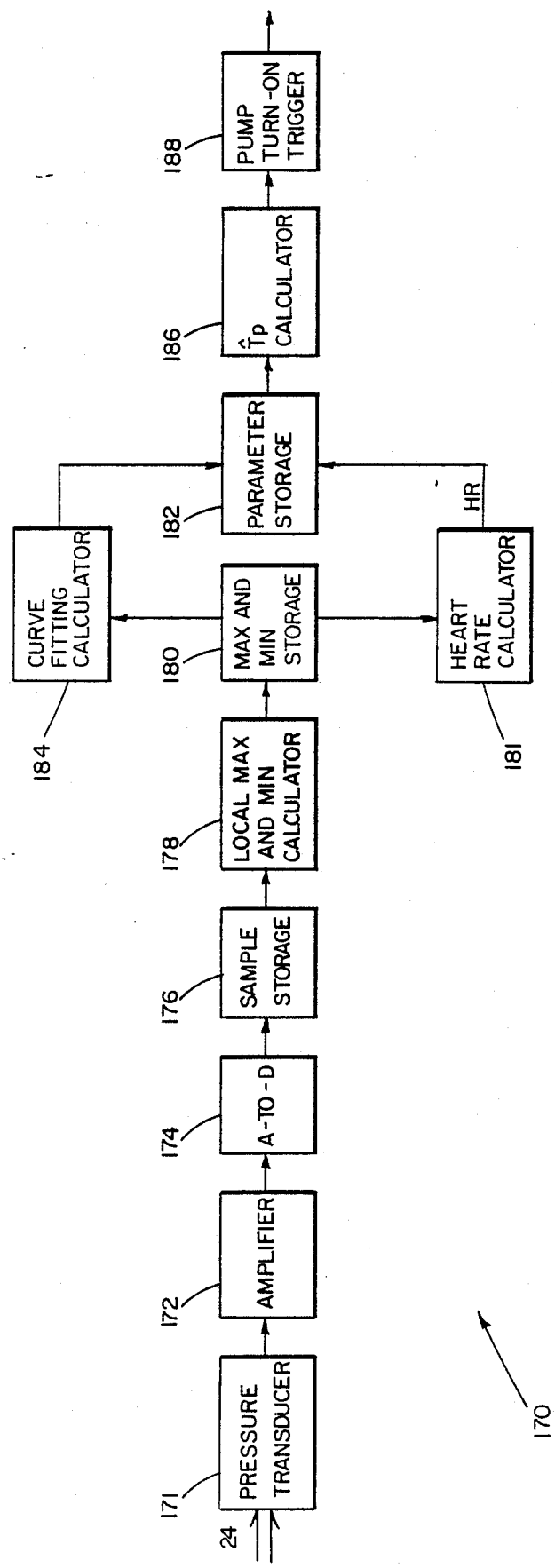
FIG. 19 is a block diagram of apparatus for performing the procedure of FIG. 18.

Referring to FIG. 19, the procedure of FIG. 1 is performed in the apparatus 170. Line 24 is connected to a pressure transducer 171 which detects the electrical signals representing coronary sinus pressure and delivers them to an amplifier 172 which in turn sends them to an A-to-D converter 174 which provides them to sample storage 176. A local max and min calculator 178 uses the stored samples to determine the local systolic maxima and diastolic minima and provides them to max and min storage 180. A heart rate calculator 181 uses the successive maximum to determine the heart rate HR which is delivered to paramater storage 182. A curve fitting calculator 184 simultaneously fits the stored max and min values to exponential curves and generates the values $A_s$, $A_d$, $T_s$, $T_d$ and delivers them to parameter storage 182. $_p$ calculator 186 then calculates $_p$ from the stored parameters and delivers its value to a pump turn-on trigger 188. Trigger 188 triggers pump turn-on at a time corresponding to the value $_p$.

Other parameters may also be used as the basis for timing the start of occlusion. For example, the frequency spectrum of the coronary sinus pressure curve during occlusion is also useful in determining $_p$. For this purpose the $_p$ calculator 186 in FIG. 19 can be arranged to perform the appropriate Fourier analysis of the CSP data to derive a frequency spectrum, and to use the spectral information as one factor in calculating In addition to predicting $_p$, the information available from the CSP curve is useful in predicting, at the beginning of intermittent occlusion, the area of the heart tissue that is at risk of dying, and at later stages of intermittent occlusion, the size of the infarcted tissue.

The area at risk is correlated to (a) the maximum local diastolic valley on the CSP curve (e.g., valley 202, FIG. 7) measured at the early stages of a period of intermittent occlusion, (b) the maximum local systolic peak on the CSP curve (e.g., peak 204, FIG. 7) measured after occlusion is interrupted (at time $t_I$) during the early stages of a period of intermittent occlusion, (c) the same as (a) but measured at the later stages of the intermittent occlusion period, and (d) the maximum local systolic peak on the CSP curve (e.g., peak 206, FIG. 7) measured during occlusion at the later stages of the intermittent occlusion period.

The infarct size is correlated to (a) the same as (c) above but taken during the later stages of the period of intermittent occlusion, (b) the maximum local systolic peak during occlusion in the middle stages of a period of intermittent occlusion, (c) the maximum local systolic valley while occlusion is interrupted during the middle stages of a period of intermittent occlusion.

Figure 20:
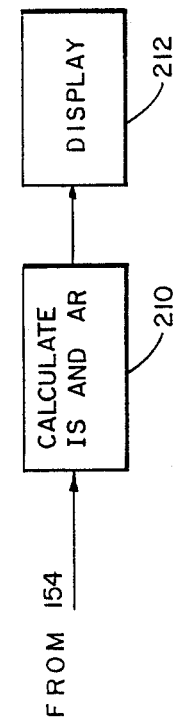
FIGS. 20, 21 show additional steps and apparatus for analyzing the area of heart tissue at risk (AR) and the size of infarcted tissue (IS).
Figure 21:
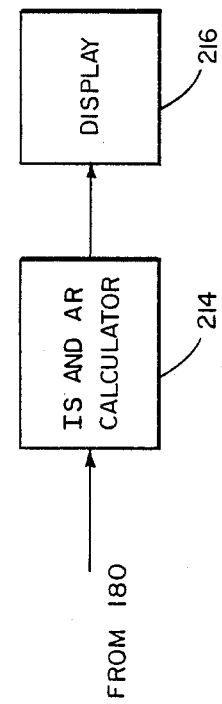

In one example of these correlations, 3 groups of dogs (28 in total) with myocardial infarction were investigated: Group I, 5 dogs with 6 hours of coronary artery occlusion (CAO); Group II, 11 dogs with 3 hours of CAO and 3 hours of reperfusion; Group III, 12 dogs with 3 hours of reperfusion. In all groups, intermittent sinus occlusion was performed, beginning at 15 minutes after CAO in Group I, 30 minutes after CAO in Group II, and 2.5 hours after CAO in Group III; and continuing in all groups during reperfusion. The maximum valley systolic and maximum peak diastolic pressures during occlusion and during the interruption of occlusion were measured shortly after the onset of intermittent occlusion (early stages), and 3 hours (middle stages) and 6 hours (later stages) thereafter. The actual area at risk (AR) and infarct size (IS) were measured using known dye solution and TTC techniques. The following correlations were demonstrated using linear and logistic stepwise regression:

$AR$ = $-0.6$ CSP Diastolic, During Occlusion (Early Stages)
 $-0.4$ CSP Systolic, Occlusion Interrupted (Early Stages)
 $+0.3$ CSP Diastolic, During Occlusion (Later Stages)
 $+0.1$ CSP Systolic, During Occlusion (Later Stages)
 $+34.5$ $r$ = $0.8\ p = 0.001$ $IS$ = $+1.4$ CSP Diastolic, During Occlusion (Later Stages
 $-0.6$ CSP Systolic, During Occlusion (Middle Stages)
 $-0.9$ CSP Systolic, Occlusion Interrupted (Middle Stages)
 $+43.8$ $r = 0.6\ p = 0.05$ Referring to FIG. 20, the procedure for deriving IS and AR values is the same as the one shown in FIG. 18 up to the point of storing the local maxima and minima except that we now also store maxima and minima for the period after interruption of occlusion. Next IS and AR are calculated 210 and then displayed 212 for analysis. Similarly, referring to FIG. 21, the apparatus is similar to that of FIG. 19 but also includes an IS and AR calculator 214 that receives its input from the min and max storage 180 and a display 216 for displaying the AR and IS values.

What is claimed is:

1. Apparatus for intermittently occluding a coronary sinus comprising
   means for occluding said sinus,
   a pressure transducer for sensing the fluid pressure within said sinus and providing corresponding fluid pressure signals, and
   a controller responsive to said transducer having means for providing trigger signals to said occluding means to trigger an occlusion and to interrupt said occlusion, said apparatus being characterized in that
   said controller includes means to estimate a plateau level of said fluid pressure during each occlusion and means to provide the trigger signal to interrupt each said occlusion on the basis of said estimate.

2. The apparatus of claim 1 wherein said controller includes means for interrupting each said occlusion before said fluid pressure reaches said plateau level.

3. The apparatus of claim 2 wherein said controller further includes means for interrupting each said occlusion before said fluid pressure reaches a predetermined percentage of said plateau level.

4. The apparatus of claim 1 further characterized by said controller comprising
   sensing means for sensing said fluid pressure signals,
   first analysis means for determining and storing a local maximum value of said pressure for each heartbeat from said stored sensed signals,
   second analysis means for estimating in real time said plateau level from said stored local maxium values, and
   comparison means for comparing a predetermined percentage of said estimated plateau level with successive said local maximum values and generating said trigger signals for triggering interruption of each occlusion at a time dependent on the result of said comparison.

5. The apparatus of claim 2 or 4 further characterized by said predetermined percentage being greater than 70% and less than 98%.

6. The apparatus of claim 5 further characterized by said predetermined percentage being about 94%.

7. The apparatus of claim 4 wherein said second analysis circuitry includes means for estimating said plateau level by fitting said stored local maximum values to an exponential curve.

8. The apparatus of claim 1 further characterized in that said occluding means comprises an inflatable element in said sinus, and a pump for selectably inflating said inflatable element in response to said trigger signals.

9. The apparatus of claim 1 further characterized in having means responsive to the volume flow in said sinus for commencing each period of occlusion of said sinus.

10. The apparatus of claim 1 further characterized in having means to display the pressure maxima for the succession of heartbeats that occurs during an occlusion to enable evaluation of the relationship of said maxima for indication of the state of health of the heart tissue.

11. The apparatus of claim 1 further characterized in having means during said occlusion to infuse a pharmacological agent into said sinus, whereby said agent can be retroperfused to heart tissue.

12. A method for intermittently occluding a coronary sinus, comprising
    providing means for occluding said sinus and for measuring the local pressure maximum within said sinus during each heartbeat,
    causing occlusion of said sinus,
    measuring the local pressure maxima for successive heartbeats during said occlusion, said method being characterized by the steps of
    estimating the plateau level of said local pressure maxima, and
    interrupting said occlusion on the basis of said estimate.

13. The method of claim 12 further comprising interrupting said occlusion before fluid pressure reaches said plateau level.

14. The method of claim 12 further comprising interrupting said occlusion when a said local pressure maximum reaches at least a predetermined percentage of said plateau level.

15. The method of claim 14 further characterized in that said predetermined percentage is at least 70% and less than 98%.

16. The method of claim 15 further characterized in that said predetermined percentage is about 94%.

17. The method of claim 12 further comprising sensing the volume flow following cessation of the preceeding occlusion period and commencing the next period of occlusion of said sinus in response to the volume flow following cessation of the preceding occlusion period.

18. Apparatus for intermittently occluding a coronary sinus comprising
    means for occluding said sinus, and
    a controller having means for providing trigger signals to said occluding means to trigger an occlusion and to interrupt said occlusion,
    said apparatus being characterized in that
    a sensor is provided for delivering flow signals indicative of the volume flow of fluid in said sinus during periods when said occlusion is being interrupted, and
    said controller includes means to trigger the initiation of the next said occlusion at a time determined by said flow signals.

19. The apparatus of claim 18 characterized in that said flow signals represent the velocity of flow of fluid in said sinus.

20. The apparatus of claim 18 wherein said sensor comprises means for determining said flow signals based on the fluid pressure in said sinus as a function of time.

21. The apparatus of claim 18 further characterized in that said controller includes
    sampling means for sampling said flow signals and storing said samples,
    analysis means for determining from said stored samples the time when the peak of said volumen flow occurs during each period of interruption of said occlusion, and
    trigger means for delivering a trigger signal to trigger the next said occlusion at a time determined by when said peak occurs.

22. The apparatus of claim 21 further comprising means for triggering said next occlusion after said peak occurs.

23. The apparatus of claim 18 further characterized in that said occluding means comprises an inflatable element in said sinus and a pump for selectably inflating said inflatable element in response to said trigger circuitry.

24. A method for intermittently occluding a coronary sinus comprising
    providing means for occluding said sinus,
    occluding said sinus, and
    thereafter interrupting said occlusion, the method being characterized by the steps of
    determining the flow within said sinus during said interruption,
    determining the time of the peak of said flow, and
    triggering the next occlusion of said sinus at a time determined by when said peak occurs.

25. Apparatus for intermittently occluding a coronary sinus comprising
    means for occluding said sinus, and
    a controller having means for providing trigger signals to said occluding means to trigger an occlusion and to interrupt said occlusion,
    said apparatus being characterized in that
    a pressure transducer is provided for sensing the fluid pressure within said sinus during said occlusion and providing corresponding fluid pressure signals, and
    said controller has means for triggering the initiation of the next said occlusion at a time based on said fluid pressure signals.

26. The apparatus of claim 25 wherein said controller further comprises means for triggering said initiation on the basis of successive pressure maxima of said fluid pressure signals.

27. The apparatus of claim 25 wherein said controller further comprises means for triggering said initiation on the basis of successive pressure minima of said fluid pressure signals.

28. The apparatus of claim 25 wherein said controller further comprises means for triggering said initiation on the basis of a combination of parameters derived from successive pressure maxima and minima of said fluid pressure signals.

29. The apparatus of claim 28 wherein said controller further comprises means for triggering said initiation on the basis of fitting said pressure maxima and said pressure minima to exponential curves.

30. The apparatus of claim 29 wherein said means for triggering includes means that trigger said initiation on the basis of a combination of parameters including the asymptotic plateaus of said exponential curves.

31. The apparatus of claim 29 wherein said means for triggering includes means that trigger said initiation on the basis of a combination of parameters including the time constants of said exponential curves.

32. The apparatus of claim 28 wherein said means for triggering includes means that trigger said initiation on the basis of a combination of parameters including heart rate.

33. A method for intermittently occluding a coronary sinus comprising
   providing means for occluding said sinus,
   occluding said sinus, and
   thereafter interrupting said occlusion,
   the method being characterized by the steps of:
   sensing the fluid pressure within said sinus during said occlusion and providing corresponding fluid pressure signals, and
   triggering the initiation of the next said occlusion at a time dependent on said fluid pressure signals.

34. The method of claim 33 further comprising causing said triggering to be dependent on successive pressure maxima and successive pressure minima of said fluid pressure signals.

35. The method of claim 34 further comprising causing said triggering to be dependent on a combination of parameters derived from said successive pressure maxima and minima.

36. The method of claim 35 further comprising causing said triggering to be dependent on fitting said pressure maxima and said pressure minima to exponential curves.

37. The method of claim 35 wherein said causing said triggering includes causing said triggering to be dependent on a combination of parameters including heart rate.

38. The method of claim 35 wherein said causing said triggering includes causing said triggering to be dependent on a combination of parameters including the asymptotic plateaus of said exponential curves.

39. The method of claim 35 wherein said causing said triggering includes causing said triggering to be dependent on a combination of parameters including the time constants of said exponential curves.

* * * * *